United States Patent
Shapiro

(10) Patent No.: US 6,562,785 B1
(45) Date of Patent: May 13, 2003

(54) METHOD FOR OVERCOMING BACTERIAL ANTIBIOTIC RESISTANCE

(75) Inventor: Howard M. Shapiro, 283 Highland Ave., West Newton, MA (US) 02465-2513

(73) Assignee: Howard M. Shapiro, West Newton, MA (US)

( * ) Notice: Subject to any disclaimer, the term of this patent is extended or adjusted under 35 U.S.C. 154(b) by 0 days.

(21) Appl. No.: 09/274,699

(22) Filed: Mar. 23, 1999

(51) Int. Cl.$^7$ .......................... A61K 38/00; A61K 38/14
(52) U.S. Cl. .......................... 514/9; 530/317; 530/320; 435/32; 435/810
(58) Field of Search .............................. 514/9; 530/317, 530/320; 435/32, 810

(56) References Cited

FOREIGN PATENT DOCUMENTS

| EP | 0 005 032 A1 | 10/1979 |
|----|--------------|---------|
| WO | WO 96/13552  | 5/1996  |

OTHER PUBLICATIONS

Roth et al., *Applied and Environmental Microbiology*, vol. 63, No. 6, pp. 2421–2431, Jun. 1997.*
Ramani et al., *Journal of Clinical Microbiology*, vol. 35, No. 9, pp. 2320–2324, Sep. 1997.*
Novo et al., *Abstract, 38$^{th}$ Annual ICAAC*, Session 44–D, paper D–43, 1998.*
Myron Sasser, "Inhibition by Antibacterial Compounds of the Hypersensitive Reaction Induced by *Pseudomonas pisi* in Tobacco", *Physiology and Biochemistry* 72, No. 12:1513–1517 (1982).
M.S. V. Pereira, et al., "Antimicrobial drug resistance in *Staphylococcus aureus* isolated from cattle in Brazil", *Letters in Applied Microbiology*, 20:391–395 (1995).
M. T. E. Suller, et al. "Fluorescence Monitoring of Antibiotic–Induced Bacterial Damage Using Flow Cytometry", *Cytometry* 35:235–241 (1999).
Y. Michel–Briand, et al., "Isolation of an antibiotic multi-resistance plasmid from *Pseudomonas aeruginosa*", *Journal of Antimicrobial Chemotherapy*, 7:371–378 (1981).
D. J. Novo, et al., "Multiparameter Flow Cytometric Analysis of Antibiotic Effects on Membrane Potential, Membrane Permeability and Bacterial Counts", *Abstracts, 38th Annual ICAAC*, Session 44–D, Paper D–43 (1998).
Rama Ramani et al., "Rapid Flow Cytometric Susceptibility Testing of *Candida albicans*", *Journal of Clinical Microbiology*, vol. 35, No. 9: 2320–2324 (Sep. 1997).
Bruce L. Roth, et al., "Bacterial Viability and Antibiotic Susceptibility Testing with SYTOX Green Nucleic Acid Stain", *Applied and Environmental Microbiology*, vol. 63, No. 6:2421–2431 (Jun. 1997).
M. Walberg and H. B. Steen, "Rapid Flow Cytometric Assessment of *E. coli* Susceptibility Towards One Quinolone and Three β–Lactam Antibiotics," *Proc. ERDEC Sci. Conf. Chem. Biol. Def. Res.* (1996), meeeting date 1995, pp. 521–526.
G. Lebek and L. Petri, "Combined Effect of Intercalating Agents and Antibiotics on R–Factor Carrying Bacteria in Broth Culture," *Infection* 7 (6) :273–274 (1979).
F. E. Hahn and J. Ciak, "Bactericidal Effects of Combinations of Amipicillin with Anti–R–Plasmid Compounds on *Salmonella typhimurium* R1$^+$," *Antimicrobial Agents and Chemotherapy*, 11(1) :176–177 (Jan. 1977).
F. E. Hahn and J. Ciak, "Elimination of Plasmidic Determinants by DNA–Complexing Compounds," *Topics in Infectious Diseases, vol. 1*, Drug Receptor Interactions in Antimicrobial Chemotherapy, Symposium, Vienna, Sep. 4–6, 1974, pp. 99–113.
D. Novo, et al., "Accurate Flow Cytometric Membrane Potential Measurement in Bacteria Using Diethyloxacarboyanine and a Ratiometric Technique," *Cytometry*, 35:55–63 (1999).

* cited by examiner

*Primary Examiner*—Christopher S. F. Low
*Assistant Examiner*—Abdel A. Mohamed
(74) *Attorney, Agent, or Firm*—Hamilton, Brook, Smith & Reynolds, P.C.

(57) ABSTRACT

The present invention is drawn to methods of killing bacteria, including antibiotic resistant bacteria, by contacting said bacteria with a membrane permeabilizing compound or combination of compounds and a membrane impermeant toxic agent or combination of agents, resulting in the death of the bacteria without substantial injury to the infected host or patient. The present invention is also drawn to compositions and kits for effecting the method of the present invention. The present invention is further drawn to methods of rendering toxic agents such as toxic organic molecules, membrane impermeant for use in the methods and compositions of the present invention.

13 Claims, No Drawings

METHOD FOR OVERCOMING BACTERIAL ANTIBIOTIC RESISTANCE

BACKGROUND OF THE INVENTION

Bacterial, fungal, and plant cells have a cell wall outside the cell membrane, while animal cells in general, and human cells in particular, do not. Compounds which interfere with synthesis of the cell wall, such as antibiotics in the penicillin and cephalosporin families, can kill bacteria without significant toxicity to an infected host or patient. It is known that rupture of the bacterial cell membrane occurs when bacteria are killed by antibiotics such as penicillin that are administered at least minimum inhibitory concentration levels; this membrane damage allows normally impermeant compounds such as propidium iodide to enter the bacteria.

There has been an alarming increase in recent years in the number of infections due to bacteria resistant to nearly all, and in some cases all available, antibiotics. Such bacteria are, by definition, not killed by the drugs. While much emphasis has been placed on the discovery of new antibiotics, it would be useful to develop methods and reagents to potentiate already existing antibiotics. In addition, such potentiating mechanisms would also be useful in combination with agents that injure bacteria but are not considered traditional antibiotic compounds. Furthermore, the treatment of other pathogens, such as fungi, is often deleterious to the host or patient due to toxicity of the therapy to the host. The potentiation of such therapy, allowing the use of lower doses of the therapeutic agent is also desirable.

SUMMARY OF THE INVENTION

The present invention relates to the discovery by the Applicant that bacteria treated with a concentration of antibiotic less than that needed to kill 100% of the organisms in culture take up propidium iodide or TO-PRO-3™ (an asymmetrical cyanine dye), although their membranes appear intact, i.e., unruptured, by virtue of their maintenance of a normal membrane potential. The subsequent growth pattern of cultures exposed to this sublethal dose of antibiotic indicates that the induced permeability was transient and reversible and that the sublethally injured bacteria eventually resumed growth. The coexistence of propidium iodide permeability and an unruptured membrane in antibiotic treated cells is a novel discovery, and raises the possibility of treating bacteria with sublethal doses of antibiotic to induce permeability to toxic agents which are impermeant, and thus harmless, to host cells.

The toxicity of most organic compounds to cells is dependent upon the compounds entering the cells; the facility with which compounds enter the cells can, in many cases, be manipulated. Both bacterial and mammalian cells are susceptible to the toxicity of the nucleic acid binding dye ethidium bromide, which shares the heterocyclic ring structure of propidium iodide but carries only a single positive charge, bearing an N-ethyl group instead of the N-propyltrimethyl (quaternary) ammonium group found in propidium iodide. Both ethidium and propidium form complexes with DNA and RNA, and are toxic to cells once taken up. However, ethidium normally enters cells, albeit slowly, while propidium is normally excluded by its additional charge.

There are many chemical modifications capable of modifying permeant organic molecules or agents to render them impermeant in addition to those described by Yue et al (U.S. Pat. No. 5,321,130 (1994) and International Application (WO96/13552)), the teachings of which are incorporated herein in their entirety. It is thus possible to prepare many derivatives of generally toxic organic molecules or agents, such as nucleic acid binding compounds, inhibitors of nucleic acid synthesis, inhibitors of protein synthesis, and inhibitors of energy metabolism, which will exhibit markedly reduced toxicity to intact mammalian and other eukaryotic cells and bacteria, but which will enter and kill bacteria or other cells such as fungi, which have been transiently permeabilized. The combination of a permeabilizing compound, such as a beta-lactam antibiotic, and a modified organic toxic agent with reduced permeability provides a novel and general therapeutic approach to treating infections by microorganisms, including those otherwise resistant to antibiotic treatment.

The phenomenon of transient membrane permeability induced by sublethal injury may be quite general. Some bacteria become dormant in the absence of nutrients and can survive for months at low or no membrane potential. Organisms in this condition have also been reported to take up dyes such as propidium and TO-PRO-3™ (Davey, H. M., Weichart, D. H., Kell D. B., Kaprelyants, A. S.: *Current Protocols in Cytometry*, Wiley-Liss, New York, 1999, 11.3.1–11.3.20.). It is probable that many antibiotics of other membrane permeabilizing compounds can induce the state of membrane permeability even in resistant organisms. Furthermore, in such dormant bacteria, it is likely that treatment with membrane impermeant toxic agents alone will result in their death.

Transient permeabilization of cell membranes with retention of viability may be induced by chemical agents such as lysolecithin or by physical agents such as electric fields (electroporation); this may be done in vitro, as for the purpose of introducing gene constructs into the cells, but is difficult or impossible to accomplish in vivo. Thus, until the present invention, there has been no incentive to develop impermeant derivatives of generally toxic agents, such as toxic nucleic acid binding compounds, inhibitors of nucleic acid synthesis, inhibitors of protein synthesis, inhibitors of energy metabolism, etc., as therapeutic agents against bacteria including gram negative bacteria such as *Pseudomonas aeruginosa*, and gram positive bacteria, such as *S. aureus* or *M. luteus*, or other pathogens, such as fungi.

The present invention provides a method of killing bacteria or other pathogens by contacting the bacteria with a membrane permeabilizing compound or combination of compounds in conjunction with an otherwise membrane impermeant toxic agent or agents. The present invention potentiates the killing effect of compounds that permeabilize bacteria or other pathogens such as fungi, including known antibiotics; this potentiation of the killing effect of antibiotics can occur even in antibiotic resistant bacteria. The present invention also provides a method to detect the presence of permeability in bacteria with intact cell membranes as evidenced by maintenance of membrane potential, allowing the detailed study of antibiotic-induced changes in bacterial physiology. The ability to differentiate among the effects of different antibiotics could lead to improvement in the treatment regimen for bacterial infection, including infection by antibiotic resistant organisms.

The present invention relates to a method of rendering pathogens such as bacteria and fungi permeable with sublethal doses of permeabilizing compounds, and thus lethally susceptible to (i.e., susceptible to killing by) a toxic agent or agents normally impermeant to, and thus inactive against, bacterial and eukaryotic cells with intact membranes.

The present invention is also drawn to a method of rendering antibiotic resistant bacteria lethally susceptible to said antibiotic or antibiotics, comprising contacting the bacteria with said antibiotic in combination with a lethal dose of an agent or agents, wherein the agent is impermeant to bacterial and eukaryotic cells with intact membranes in the absence of the antibiotic, resulting in the death of the bacteria. The present invention is further drawn to a method of preventing survival or generation of antibiotic resistant bacteria. This method comprises contacting the bacteria with a combination of said antibiotic or antibiotics at a concentration sufficient to permeabilize said bacteria and a lethal amount of an agent or agents, wherein the agent is impermeant to bacterial and eukaryotic cells with intact membranes in the absence of the antibiotic, resulting in the death of the bacteria. The present invention also relates to a method of killing bacteria comprising contacting said bacteria with a sublethal dose of an antibiotic or antibiotics in combination with a lethal amount of an agent or agents, wherein said agent is impermeant to bacterial and eukaryotic cells with intact membranes in the absence of the antibiotic, resulting in the death of the bacteria.

The present invention is further drawn to a method of rendering a generally toxic agent (e.g., an agent toxic to bacteria and eukaryotic cells) impermeant to bacterial and eukaryotic cells with intact membranes for use as a bactericidal agent against permeabilized bacteria.

The present invention is also drawn to both pharmaceutically and physiologically acceptable compositions comprising bacterial cell permeabilizing compounds and toxic agents, wherein the agent(s) are impermeant to bacterial and eukaryotic cells with intact membranes. Said permeabilizing compound is present in the composition in an amount sufficient to render the bacteria lethally susceptible to the agent(s) present in the composition.

The present invention is also related to both pharmaceutical and physiologically acceptable compositions comprising a bacterial cell permeabilizing compound or compounds and a modified organic toxic agent or agents. The modified organic toxic agent is impermeant to bacterial and eukaryotic cells with intact membranes, and the permeabilizing compound is present in an amount sufficient to render the bacterial lethally susceptible to the toxic agent.

The present invention is also drawn to kits for killing bacteria. These kits comprise a bacterial cell permeabilizing compound and a toxic agent, wherein the agent is impermeant to bacterial and eukaryotic cells with intact membranes in the absence of the permeabilizer.

The present invention is further drawn to methods for selecting bacteria-permeabilizing compounds. The method comprises exposing bacteria to a cell impermeant toxic agent or toxic agent in the presence or the absence of a test compound and measuring bacterial viability. In this method, decreased viability in the presence of the test compound is indicative of a bacteria-permeabilizing compound.

The present invention is also drawn to methods for selecting a bactericidal toxic agent, wherein the toxic agent is impermeant to bacterial and eukaryotic cells with intact membranes in the absence of a membrane permeabilizing agent. The method comprises contacting the bacteria with a test toxic agent in the presence or absence of a cell-permeabilizing compound, and measuring bacterial viability. In this method, decreased cell viability in the presence of the permeabilizing compound is indicative of a cell-impermeant toxic agent.

The present invention demonstrates that bacteria permeabilizing compounds, including antibiotics, can be potentiated to kill bacteria at concentrations below the minimal inhibitory concentration (MIC) including bacteria that are otherwise resistant to killing by said antibiotic or permeabilizing agent.

DETAILED DESCRIPTION OF THE INVENTION

The cells of living organisms are surrounded by a cell membrane, composed primarily of two layers of phospholipids. When intact, this membrane prevents certain classes of chemical compounds from entering the cell. Compounds which can readily cross the membrane and enter or leave the cell are said to be membrane permeant, or permeant. Membrane impermeant, or impermeant, compounds are those which are excluded by the intact membrane when outside the cell, and/or which are retained by the membrane when formed inside the cell by intrinsic metabolic activity or by intracellular transformation of administered permeant compounds into impermeant compounds.

Although there are differences among cells in permeability to some compounds, it is widely believed that certain classes of compounds, including organic compounds bearing at least two positive charges and most negatively charged organic compounds, are impermeant to the cells of bacteria, protists, fungi, plants, and animals. The demonstration, by microscopy or by instrumental techniques such as flow cytometry (Shapiro, H. M., Practical Flow Cytometry, 3rd Ed., New York, Wiley-Liss, 1995), of uptake of such compounds by cells is generally considered to indicate cell death. Among the compounds used as indicators of cell death are fluorescent nucleic acid binding dyes with two or more positive charges, such as propidium iodide (PI), TO-PRO-3™ and SYTOX GREEN™ (an asymmetrical cyanine dye), (Molecular Probes, Inc., Eugene, Oreg.).

In bacterial and eukaryotic cells with intact membranes, there is typically a difference of electrical potential across the cell membrane, with the interior negative by between 5 and 200 mV with respect to the exterior. This membrane potential is generated by differences in concentrations of inorganic ions, to which membrane permeability is restricted, inside and outside the membrane. Membrane potential will be reduced to zero if the membrane develops holes large enough to permit inorganic ions to cross freely, as may occur when cells are killed by heating or by freezing and thawing; under these circumstances, the membrane typically becomes permeable to dyes such as propidium iodide. Several classes of chemical compounds can also alter membrane potential; these include ionophores, which carry inorganic ions through the membrane or form channels in the membrane allowing inorganic ions to pass through readily. In bacteria, administration of a proton ionophore such as carbonyl cyanide-m-chlorophenylhydrazone (CCCP) will reduce membrane potential to zero, but leave the membrane impermeable to dyes such as propidium iodide.

Prior to the present invention, it was expected that doses of antibiotics sufficient to induce bacterial membrane permeability to dyes such as propidium iodide and TO-PRO-3™ would cause cell death, with concomitant loss of membrane potential. The present invention demonstrates that the mechanism of action of antibacterial agents is more complex than commonly perceived.

The increase in membrane permeability to impermeant nucleic acid dyes in cell populations exposed to beta-lactam antibiotics at concentrations at or above the MIC (minimal inhibitory concentration) is a well-known phenomenon (Roth, B. L. et al., *Appl. Env. Microbiol.* 63(6):2421–31 (1997)). It is also well known that concentrations of beta-lactams below MIC cause the formation of giant, multicellular structures, as a consequence of incomplete bacterial fission (Lorian, V. and Gemmel, C. G., In: Antibiotics in Laboratory Medicine, 3rd ed.; Lorian V (eds) Williams & Wilkins, Baltimore, 1991, pp. 493–555). The present invention demonstrates the surprising result that sub-MIC levels of an antibiotic transiently permeabilize cells without affecting membrane potential, indicating that these compounds and other membrane permeating compounds are useful to injure bacteria and render them lethally susceptible to a toxic agent that is normally membrane impermeant.

Several authors have attempted to examine the effects of antibacterial agents on several different cellular characteristics or parameters, including membrane permeability, membrane potential (MP) and respiratory activity (Yeaman, M. R. et al., *J. Clin. Invest.* 101:178–87, 1998 and Mason D. J. et al., *Antimicrob. Ag. Chemother.* 39(12):2752–8, (1995)). However, in these studies, only one of the parameters was measured in any given aliquot of sample, making it impossible to detect and correlate changes in two or more parameters on a cell-by-cell basis.

It is usually assumed that bacterial permeability to nucleic acid dyes such as TO-PRO-3™, PI, and SYTOX GREEN™ is associated with the presence of substantial, irreparable breaches in the membrane, in the presence of which the organisms cannot maintain a membrane potential and are, therefore, non-viable (Roth, B. L., et al., *Appl. Env. Microbiol.* 63(6):2421–31, (1997)). However, the Applicant performed flow cytometric studies in which membrane potential (MP) and permeability to TO-PRO-3™ were measured in the same cells at the same time, which revealed that bacteria exposed to concentrations of amoxicillin below MIC always produced a transiently membrane permeant population with a normal MP, with eventual increases in bacterial counts coincident with a reversion to a single, impermeable population. While not wishing to be bound by theory, there are two possible bases for this observation. The first is that the TO-PRO-3™ permeable cells are dead or dying, and that the TO-PRO-3™-impermeable, viable population with a normal MP expands over the course of the following two hours until it comprises the majority of the cells. The second is that cells become transiently permeable to TO-PRO-3™, due to amoxicillin treatment, but can repair the damage and can continue dividing once a permeability barrier has been restored.

The kinetics of the disappearance of the permeable population suggest that the injured cells do, in fact, revert to an impermeable state and resume growth. It has been suggested that such a transition from a permeable to an impermeable state is responsible for the lag period before growth is observed following the addition of nutrients to dormant, starved cultures of *Micrococcus luteus* (Tatyana, V. et al., *Appl. Environ. Microbiol.* 60(9):3284–91 (1994)). Thus, dormant bacteria, such as nutrient starved *M. luteus* or spore-like bacteria, such as the elementary body form of Chlamydia, are susceptible to the method of the present invention, possibly without permeabilization.

Concentrations of amoxicillin at or above MIC, in contrast to those below MIC, produced both increased permeability to TO-PRO-3™ and loss of membrane potential. Given the apparently transient nature of permeabilization, on the one hand, and the relative difficulty of interpreting TO-PRO-3™ fluorescence measurements, on the other, it seems that in amoxicillin-treated cells, loss of membrane potential is a more reliable indicator of cell death than is membrane permeability. Yet this permeabilization of the bacteria can be taken advantage of to kill the bacterial cell.

The method of the present invention should be useful for studying antibiotic-induced changes in bacterial physiology. Simultaneous assessment of changes in two or more physiological characteristics allows distinctions to be made between the mechanisms of actions of different classes of antimicrobial agents. Application of multiparameter flow cytometry can provide valuable information about the pharmacology of existing and newly developed antibiotics. The recently described ratiometric technique for membrane potential measurement should be extremely useful for these types of studies, because it corrects for variations in cell size, including those resulting from the action of antibiotics (Novo et al., *Cytometry* 35:55–63, 1999).

Furthermore, the present invention provides methods, compositions and kits for the potentiation of bacterial permeabilizing compounds, such that these compounds, in the presence of an otherwise impermeant toxic agent, are capable of killing bacteria without injuring the infected host or patient. These compounds can be any membrane permeabilizing compound specific for bacteria or other pathogens, such as fungi, including cell wall synthesis inhibitors and antibiotics. The present invention further provides a method to select permeabilizing compounds as well as toxic agents. Finally, the present invention provides a method for rendering known toxic organic molecules membrane impermeant. These permeabilizing compounds, toxic agents and modified toxic agents are useful in the method of the present invention.

The methods, compositions and kits of the present invention are generally applicable to any pathogen that can be selectively permeabilized over the host or patient's cell. For example, the present invention is also useful in the therapy of other pathogenic infections such as mycotic (fungal) infections. It has been shown that fungal cells damaged by antifungal agents take up propidium iodide (Green, L. et al., *J Clin Microbiol* 32:1088–91 (1994)); Ramani, R. et al. *J. Clin Microbiol* 35:2320–4 (1997). Amphotericin B, the primary drug used to treat systemic mycotic infections, is known to form channels in the fungal cell membrane. Although newer formulations have improved the therapeutic index, the toxicity of amphotericin B is high, and the use of normally impermeant toxins in combination with such permeabilizing compounds enables the dose to be reduced, thus potentiating the mycotoxicity of the permeabilizing compounds.

The present invention relates to a method of rendering bacteria lethally susceptible to an agent. In this method, the bacteria are rendered permeant to a lethal dose of the agent, wherein the agent is normally impermeant to bacterial and eukaryotic cells with intact membranes. Bacterial cells can be rendered permeant by any suitable means. In one embodiment, the bacteria are contacted with an effective amount of a membrane permeabilizing compound, wherein said compound selectively permeabilizes bacterial cells. The amount of permeabilizing agent required to permeabilize bacteria can be readily determined using methods well known in the art. Compounds capable of permeabilizing bacteria in vitro are expected to have the same effect in an infected host or patient, where the host or patient is any multicellular eukaryotic organism, especially mammals, and including humans. For example, the compound can be used at a concentration of about 1% of the MIC to about 90% of the MIC, wherein the MIC is defined for non-resistant bacteria. Minimal inhibitory concentrations for a number of compounds are well known in the art as published for example, in the Physician's Desk Reference, the Merck Index, or in the Material Safety Data sheets provided by commercial sources of the compounds. In addition, the MIC can be determined using techniques well known in the art. A concentration of permeabilizer greater than the MIC may be used, in particular for drug resistant bacteria. However, treatment would be less costly if lower doses of the permeabilizing compound were used.

In one embodiment of the present invention, the permeabilizing compound is a cell wall synthesis inhibitor. In another embodiment, the permeabilizing compound is an antibiotic. Useful cell wall synthesis inhibitors and antibiotics are well known in the art and include compounds such as cycloserine, vancomycin, bacitracin, β-lactams, cephalosporins, monobactams and carbapenems.

Methods for measuring cell permeation are well known in the art including commercially available kits. The permeability of cells can be tested using dyes that are normally excluded by intact cells. Such dyes are well known in the art and can be commercially obtained along with instructions for such use.

In one embodiment of the present invention, the toxic agent has 2 or more positive charges, e.g., propidium iodide and SYTOX GREEN™. In a more specific embodiment, the agent binds nucleic acid. Several examples of membrane impermeant nucleic acid binding agents that can be lethally toxic to cells are well known in the art and include compounds such as acridine, thiazine, and phenanthridinium compounds and symmetric and asymmetric cyanine dyes and homo- and heterodimers thereof. Examples of agents contemplated by the present invention are acridine homodimer, ethidium acridine, ethidium bromide, ethidium diazide, ethidium homodimer, ethidium monoazide, SYTOX GREEN™, and TO-PRO-3™ (Molecular Probes Catalogue, Molecular Probes, Eugene, Oreg. and International Application (WO96/13552)). Examples of such agents are shown below.

toxicology information or by a standard mutation analysis such as the Ames test. As an upper limit, data is also available or can be measured using routine techniques for determining $LD_{50}$ in animal models.

The present invention also relates to a method of killing bacteria. In this method, the bacteria are contacted with a sufficient amount of bacteria permeabilizing compound as described above, in combination with a lethal amount of an agent, wherein said agent is impermeant to bacterial and eukaryotic cells with intact membranes in the absence of the permeating compound. Suitable agents are well known in the art and described above.

In one embodiment of the present invention, the pathogen is contacted with the permeabilizing and the toxic agent simultaneously. In another embodiment of the present invention the pathogen is first contacted with the permeabilizing compound and then with the toxic agent. The permeabilized pathogen maybe contacted with the toxic agent up to about 4 hours after permeabilization. Similar to antibiotic therapy, in another embodiment of the present invention, the host or patient can be treated continuously with the permeabilizing agent, to maintain the desired level of permeabilizing agent within the host. The toxic agent can then be added simultaneously, in intermittent doses or contiuously as with the permeabilizing agent. In yet another embodiment, the pathogen is contacted with the toxic agent before contact with the permeabilizing compound.

The present invention is also drawn to a method of rendering antibiotic resistant bacteria lethally susceptible to said antibiotic. In this method the bacteria are contacted with said antibiotic in combination with a lethal amount of an agent, while the agent is impermeant to bacterial and eukaryotic cells with intact membranes in the absence of the antibiotic, resulting in the death of the antibiotic resistant cells. The present invention is further drawn to a method of preventing survival or generation of antibiotic resistant bacteria. This method comprises contacting the bacteria with

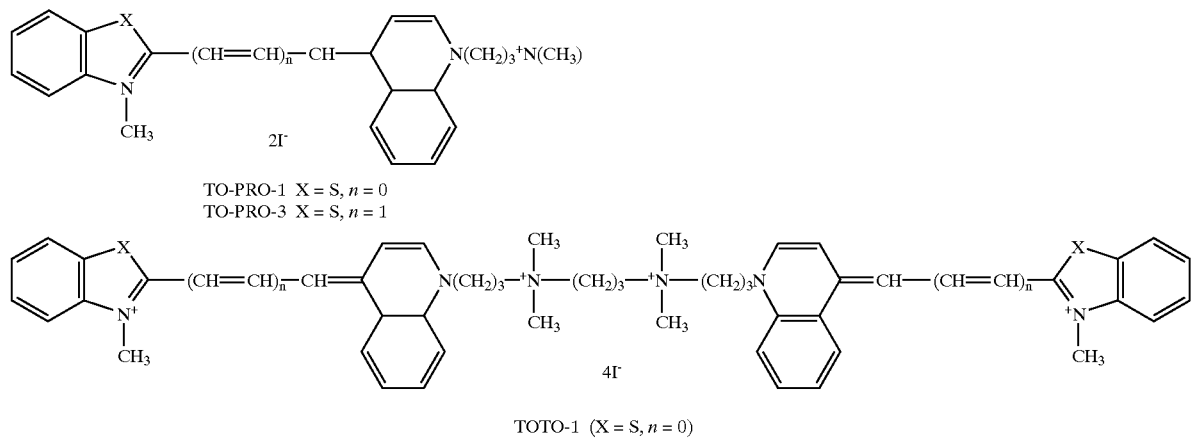

TO-PRO-1 X = S, $n$ = 0
TO-PRO-3 X = S, $n$ = 1

TOTO-1 (X = S, $n$ = 0)

In other embodiments of the invention, the agent is, respectively, an inhibitor of nucleic acid synthesis, an inhibitor of protein synthesis, or an inhibitor of energy metabolism. It is well within the ability of one of ordinary skill in the art to determine the amount of a specific toxic agent to use in the methods and compositions of the present invention using routine screening techniques and published toxicology information. For example, the lower limit of a toxic agent would be that which causes mutation in the bacteria or pathogen of interest. This can be determined from published a combination of said antibiotic, at a concentration sufficient to permeabilize said bacteria, together with a lethal amount of an agent, when the agent is impermeant to bacterial and eukaryotic cells with intact membranes in the absence of the antibiotic, resulting in the death of the bacteria. Permeabilizing agents are well known in the art as described above.

As used herein, agent, toxin, toxic agent or toxic molecule refers to any type of molecule, manmade or naturally derived, that once inside the cell in sufficient quantity, is capable of killing the cell. Organic molecules are especially useful in the present invention. Further, said agent, toxin, agent, toxic agent or toxic molecule either is or can be made membrane impermeant, using techniques well known in the art.

Agents useful in killing the permeabilized bacteria are also well known in the art and include nucleic acid binding compounds such as acridines, thiazines, phenanthridinium compounds such as propidium iodide, and symmetrical and asymmetrical cyanine dyes, and also inhibitors of nucleic acid synthesis, inhibitors of protein synthesis, and inhibitors of energy metabolism, as described above. The present invention also relates to a method of killing bacteria comprising contracting said bacteria with a sublethal dose of an antibiotic in combination with a lethal amount of an agent, wherein said agent is impermeant to bacterial and eukaryotic cells with intact membranes in the absence of the antibiotic, resulting in the death of the bacteria. The present invention is drawn to a method of potentiating the effect of antibiotics even on antibiotic resistant cells.

The present invention is also drawn to a method of generating toxic agents useful in the present invention. Known toxic agents can be rendered impermeant to bacterial and eukaryotic cells with intact membranes using methods well known in the art. In one embodiment of the present invention, a toxic agent bearing a single positive charge is modified by the substitution of a side chain containing a quaternary ammonium group for an N-alkyl group, giving the modified agent two positive charges. In a further embodiment of the present invention, the toxic agent is a nucleic acid binding compound.

In U.S. Pat. No. 5,321,130 (1994) and International Application (WO96/13552), the teachings of which are incorporated herein in their entity, S. T. Yue et al., developers of TO-PRO-3™ and SYTOX GREEN™ at Molecular Probes, Inc., disclose a variety of methods for manipulating the permeancy of asymmetric cyanine nucleic acid binding dyes, one of their objectives being to develop reliable probes of membrane integrity for assessment of cell viability and/or cell death. The parent cyanine dyes, with a single, delocalized positive charge, are permeant to most cell types, including mammalian cells; the replacement of N-alkyl substituents by a structure(s) including a quaternary ammonium group creates compounds with double, triple, etc. positive charges, which are impermeant. Each quaternary ammonium group is balanced by a biologically compatible counterion, where a substance that is biologically compatible is not toxic as used, and does not have a substantially deleterious effect on biomolecules. Examples given include chloride, bromide, iodide, sulfate, and perchlorate.

The present invention is also drawn to both pharmaceutically and physiologically acceptable compositions comprising bacterial cell or pathogen permeabilizing compounds and toxic agents, wherein the agents are impermeant to bacterial and eukaryotic cells with intact membranes. Said permeabilizing compounds are present in the composition in an amount sufficient to render the bacteria or pathogen lethally susceptible to the agents present in the composition. The present invention is also related to compositions comprising a bacterial cell or pathogen permeabilizing compound and a modified organic toxic agent. The modified organic toxic agent is impermeant to bacterial and eukaryotic cells with intact membranes. The permeabilizing compound is present in an amount sufficient to render the bacteria or pathogens lethally susceptible to the toxic agent present in the composition. The permeabilizing compound and toxic agent can be provided together or separately in a pharmaceutically or physiologically acceptable carrier. The composition can be in any suitable form for administration to a patient or a host, for example, in liquid, capsule, ointment or suppository form, such that it may be administered by injection, ingestion or application. Pharmaceutically or physiologically acceptable carriers are well known in the art.

The present invention is also drawn to kits for use in killing bacteria. These kits comprise a bacterial cell or pathogens permeabilizing compound and a toxic agent, wherein the agent is impermeant to bacterial and eukaryotic cells with intact membranes in the absence of the permeabilizer.

The present invention is further drawn to methods for selecting bacteria or pathogens permeabilizing compounds. The method comprises exposing bacteria to a cell or pathogen impermeant toxic agent in the presence or the absence of a test compound and measuring viability of the treated cells. Viability can be measured using methods well known in the art. In this method, decreased viability in the presence of the test compound is indicative of a bacterial permeabilizing compound. Viability can be measured using commercially available viability assays, or by standard culture methods well known in the art. For example, the bacterial concentration can be determined using the technique described in Example 1.

The present invention is also drawn to methods for selecting a bacterial or pathogen toxic agent, wherein the toxic agent is impermeant to bacterial and eukaryotic cells with intact membranes in the absence of a membrane permeabilizing agent. The method comprises contacting the bacteria or pathogen with a test toxic agent in the presence or the absence or a cell permeabilizing compound, and measuring viability of the treated cells. As described above, viability can be measured using methods well known in the art. In this method, decreased cell viability in the presence of the permeabilizing compound is indicative of a cell impermeant toxic agent.

The teachings of the references cited herein are incorporated herein by reference, in their entirety. Furthermore, as described above, the method of the present invention is applicable to the killing of other pathogens, such as fungi, where said pathogens are selectively permeabilized over the host cells, allowing an otherwise impermeant toxic agent to enter and kill the pathogen.

EXAMPLES

Example 1

Measuring Membrane Potential (MP), Membrane Permeability and Cell Number

The membrane potential-sensitive dye diethyloxacarbocyanine iodide (DiOC2(3)) was obtained from Accurate Chemical (Hicksville, N.Y.); the membrane permeability indicator TO-PRO-3™ was obtained from Molecular Probes (Eugene, Oreg.). The proton ionophore carbonyl cyanide m-chlorophenylhydrazone (CCCP) was obtained from Sigma (St. Louis, Mo.). CCCP reduces bacterial membrane potential to zero by dissipating the transmembrane proton gradient. Cells incubated in the presence and absence of CCCP, respectively, show high and low ratios of red to green DiOC2 (3) fluorescence. The antibiotics amoxicillin, chloramphenicol, erythromycin, streptomycin, and tetracycline were obtained from Sigma (St. Louis, Mo.).

Flow cytometric studies were performed using a laboratory-built dual laser instrument optimized for bacterial analysis. DiOC2(3) was excited at 488 nm by a beam from an argon ion laser; its green fluorescence was detected through a 530 nm, 20 nm bandwidth bandpass filter, and its red fluorescence was detected through a 610 nm, 19 nm bandpass filter. TO-PRO-3™ was excited at 633 nm by a beam from a helium-neon laser, and its fluorescence was detected through a 695 nm long pass filter. Light scattered at small angles to the 488 nm beam (forward scatter) was used as the trigger signal. Sheath flow rate was 10 ml/min; sample analysis rate was kept below 1,000 events/second. The signal pulse amplitudes were captured by high-precision peak detectors, and digitized using an Analogic HSDAS-16 16-bit data acquisition system in a Pentium-class personal computer. Software was used to perform logarithmic conversion on all of the parameters, which were represented on a 256-channel, 4-decade logarithmic scale.

*Staphylococcus aureus* (ATCC 29213) and *Micrococcus luteus* were grown overnight in trypticase soy broth. Stock solutions of antibiotics were made according to Anhalt & Washington (1991)(Balows, A. et al, (eds) American Society for Microbiology, Washington, 1991, pp. 1199–200). Antibiotics were diluted to the appropriate concentration in 1 ml of Mueller-Hinton broth (Gibco, Gaithersburg, Md.), and filtered though a 0.22 $\mu$m filter (Gelman Sciences, Ann Arbor, Mich.). MIC was defined as the minimum concentration of antibiotic that caused no growth after 24 hours in Mueller-Hinton broth.

Bacteria were added to an antibiotic solution at a concentration of $5.5 \times 10^5$/ml and incubated for the appropriate amount of time at 37 degrees C. while shaking. At each time point, a 500 ml aliquot was removed and 30 $\mu$M DiOC2(3) and 100 nM TO-PRO-3™ were added simultaneously. The bacteria were allowed to incubate with the dye for 4 minutes prior to flow cytometric analysis. A second 500 ml aliquot was treated identically, except that CCCP (final concentration 15 $\mu$M) was added to electrically depolarize the bacteria (i.e., to reduce membrane potential to zero).

Membrane potential was determined as a ratio of red to green DiOC2(3) fluorescence, providing a cell size-independent measure of MP. To measure membrane permeability, 100 nM TO-PRO-3™ was used in conjunction with the MP dye, DiOC2(3). TO-PRO-3™ exhibits substantially increased fluorescence on binding to intracellular nucleic acids; it is excluded from cells with intact membranes, while staining nucleic acids in cells with damaged membranes (Haugland, R P, In: Handbook of Fluorescent Probes and Research Chemicals, 6th ed. Molecular Probes Inc, Eugene, Oreg., 1996, pp. 144–78). Cells killed by heat exposure (100 degrees C. for 10 minutes) were used as positive controls for TO-PRO-3™ staining.

Bacteria were counted by adding 4 $\mu$M sky blue beads (Spherotech, Libertyville, Ill.) to the cell suspension at a known concentration, determined by counting on a haemocytometer. A working solution of $1 \times 10^7$ beads/ml in water containing 0.5% Triton X-100 was made daily. Beads were diluted 1:100 into the bacterial sample and could be identified and counted based on their intense fluorescence (excitation at 633 nm; emission above 695 nm). The volume of sample analyzed in any given aliquot was calculated from the number of beads measured; dividing the number of bacteria by this volume yielded the concentration of bacteria in the aliquot.

Example 2

Effect of Antibiotics on MP and Membrane Permeability

Although 4 $\mu$g/ml chloramphenicol completely prevented bacterial growth, no changes in either MP or permeability were observed after 4 hours. Mortimer et al. have also shown that chloramphenicol does not cause changes in permeability, even at high concentrations. Since chloramphenicol works by binding to the 50S subunit of the ribosome and inhibiting the interaction between the aminoacyl-tRNA and the ribosome, interfering with protein synthesis, (Mortimer, F. C. et al., Cytometry 1998; Suppl 9:CT57, 1998), it appears that de novo protein synthesis is not needed for the maintenance of MP or permeability, at least for a four hour period.

Tetracycline (MIC 0.25 $\mu$g/ml) and erythromycin (MIC 4 mg/ml) produced concentration- and time-dependent depolarizations; 4 $\mu$g/ml of either drug reduced MP to −50 mV after 4 hours. Concentrations of these drugs below 1 $\mu$g/ml did not cause any permeability changes; however, after 4 hours exposure to 4 $\mu$g/ml, 50% and 20% of tetracycline- and erythromycin-treated bacteria, respectively, were stained by TO-PRO-3™, indicating that membranes were rendered permeable to this molecule. It is well known in the art that tetracycline and erythromycin inhibit protein synthesis by binding to the ribosome on the 30S and 50S subunits, respectively. However, since the studies with chloramphenicol showed that protein synthesis is not necessary for the maintenance of either MP or permeability, it is possible that that tetracycline and erythromycin may have more direct effects on the cell membrane. It is known that sub-inhibitory concentrations of erythromycin can induce alterations in the outer membrane (Tateda, K. et al., *J. Antimicrob. Chemother.* 34:931–42, 1994 and Brenciaglia, M. I. et al., *Microbiologica* 283–8, 1995); however, it is unlikely that this occurred in the present example, as permeability changes were only induced by concentrations above MIC.

Effects of amoxicillin (MIC 2 $\mu$g/ml) were strongly concentration-dependent. If concentrations below MIC were used, the bacteria drastically increased in size, as seen by microscopic examination and large increases in the forward scatter signal. Changes in permeability could be observed 45 minutes after antibiotic addition; however, the variance of the TO-PRO-3™ fluorescence distribution was quite large, due primarily to the large variance in size resulting from drug administration. The raw TO-PRO-3™ fluorescence data was corrected for size variation by calculating a quantity proportional to the logarithm of the ratio of TO-PRO-3™ fluorescence to green DiOC2(3) fluorescence, which is known to be proportional to size; the logarithm of green fluorescence was subtracted from the logarithm of TO-PRO-3™ fluorescence, and a constant was added to keep the values on scale. This allowed cells which had become permeable to TO-PRO-3™ to be visualized as a discrete population. Thus, when the size of the bacteria is altered by the permeabilizing agent, such as β-lactam antibiotics used at concentrations below MIC, correction for change in cell volume is important in making permeability measurements. After 2 hours of amoxicillin treatment at either 0.25 or 0.5 $\mu$g/ml, a population that was permeable to TO-PRO-3™, but that maintained a normal MP, was detected. After four hours, the majority of the cells regained their membrane integrity. Resumption of bacterial growth was coincident with this reversion to a TO-PRO-3™-impermeable state, which occurred after 3 hours in the presence of 0.25 $\mu$g/ml amoxicillin and after 4 hours in the presence of 0.5 $\mu$g/ml. In contrast to what was observed with amoxicillin concentrations below MIC, the dominant characteristic of cells treated with concentrations above MIC was a loss of MP. Bacteria exposed to a 4 $\mu$g/ml consistently had lower percentages of cells permeable to TO-PRO-3™ than did those exposed to 1 $\mu$g/ml.

In cells exposed to amoxicillin at concentrations above MIC, DiOC2(3) staining revealed a population with MP intermediate between those observed in intact and CCCP-treated cells; after a longer period of time, this population decreased in size, apparently being replaced by a population of fully depolarized cells. Use of a ratiometric MP dye is particularly useful. Once size is corrected for using the DiOC2(3) fluorescence measurement value (Novo, D et al., Cytometry 35:1–9, 1999), it becomes evident that the majority of cells have maintained their membrane integrity. Concentrations of amoxicillin above MIC, in contrast to those below, produced both permeability increases and loss of MP.

Example 3

Compounds that Affect MP with Little or No Effect On Permeability

Streptomycin (5 µg/ml) reduced MP by 1 hour (the earliest time point), and MP remained reduced at 105 minutes and 4 hours. No permeability changes were seen. The effect of streptomycin on MP was abolished if organisms were preincubated with 1 mg/ml erythromycin for 30 minutes.

Streptomycin is the prototype of the aminoglycosides, a class of antibiotics for which the mechanism of action is incompletely understood (Davis, B, *Microbiol. Rev.* 51(3):341–50, 1987). The major site of action of the aminoglycosides is the ribosome, where it is thought that the drugs block the initiation of protein synthesis and also cause misreading in protein translation (Davis, B., Microbiol Rev 51(3):341–50, 1987). However, a secondary effect of the aminoglycosides is membrane damage (Davis, B., Microbiol. Rev. 51(3):341–50, 1987). Some authors have reported that membrane damage depends on de novo protein synthesis (Hancock, R E et al., Antimicrob. Agents. Chemother. 19:777–85, 1981), noting that is prevented by pretreatment with chloramphenicol. Others claim that membrane damage is not dependent on active protein synthesis, as damage is evident within 1 minute of gentamicin treatment, and occurs in the presence of metabolic inhibitors (Martin, N L and Beveridge, T J, Antimicrob. Agents. Chemother., 29(6):1079–87, 1986). However, whatever the exact mechanism of membrane damage, streptomycin did not increase membrane permeability, as seen by the failure of treated bacteria to stain with TO-PRO-3. Other authors show no (Siegel, S A et al., Infect. Immun. 61(2):512–9, 1993), or very small (Mortimer, F C et al., Cytometry, Suppl 9:CT57, 1998), changes in permeability to nucleic acid stains, as detected by flow cytometry, induced by the aminoglycoside antibiotic gentamicin in gram negative organisms, even at concentrations up to 10 times MIC. Since aminoglycosides are known to increase membrane permeability to a variety of small molecules including nucleotides, citrate and amino acids (Davis, B, Microbiol. Rev. 51(3):341–50, 1987), the lack of staining by nucleic acid dyes suggests that a different pathway of membrane damage by aminoglycosides might be involved in making cells permeable to the dyes, or that a greater degree, or different type, of permeability is needed to permit entry of these dyes.

Streptomycin did reduce MP, as others have reported previously (Mason, D J et al., *J. Microsc* 176:8–16, 1998). Streptomycin is known to cause K+ efflux and inhibit respiration (Hancock, R E, J. Antimicrob. Chemother. 8:429–45, 1981), both of which should lead to loss of MP. Chloramphenicol has been shown to prevent streptomycin induced cell death (Davis, B, Microbiol. Rev. 51(3):341–50, 1987), and chloramphenicol, tetracycline and erythromycin all prevent membrane blebbing and damage (Iida, K and Koike, M,*Antimicrob. Agents. Chemother.* 5:95–7, 1974 and Hancock, R E et al., Antimicrob. Agents. Chemother. 19:777–85, 1991). The streptomycin-induced loss of MP was prevented by erythromycin suggesting that active protein synthesis is required for the effect on MP. The reduced level of MP was maintained from 105 minutes to 4 hours, suggesting that the damage is not cumulative and that the streptomycin-treated organism still maintains a partial ability to regulate its MP.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of killing a pathogen with a toxic agent, comprising; contacting said pathogen with a permeabilizing compound and with a lethal amount of said toxic agent, wherein said lethal amount of toxic agent is impermeant to pathogen and host cells in the absence of the permeabilizing compound and said lethal amount of toxic agent is only toxic upon entry into the pathogen, and wherein the permeabilizing compound permeabilizes pathogen but not host cells and is present in an amount sufficient to transiently permeabilize the pathogen such that the pathogen maintains membrane potential, thereby allowing the lethal amount of toxic agent to enter and kill the transiently permeabilized pathogen.

2. The method of claim 1, wherein the pathogen is contacted with a combination of membrane impermeant agents.

3. The method of claim 1, wherein the pathogen is contacted with a combination of pathogen permeabilizing compounds.

4. The method of claim 1, wherein the pathogen is selected from the group consisting of: bacteria and fungi.

5. The method of claim 1, wherein the pathogen permeabilizing compound is a cell wall synthesis inhibitor.

6. The method of claim 1, wherein the toxic agent binds nucleic acid.

7. The method of claim 1, wherein the pathogen permeabilizing compound is present at about 1 to about 90% of said compound's minimal inhibitory concentration.

8. The method of claim 7, wherein the pathogen permeabilizing compound is selected from the group consisting of: cycloserine, vancomycin, bacitracin, β-lactams, cephalosporins, monobactams and carbapenems.

9. A method of killing antibiotic resistant bacteria with a toxic agent comprising; contacting the antibiotic resistant bacteria with a combination of antimicrobial agent and a lethal amount of said toxic agent, wherein the antimicrobial agent permeabilizes bacterial but not non-bacterial cell and is present in an amount sufficient to transiently permeabilize the bacteria such that the permeabilized bacteria maintain membrane potential, and wherein the lethal amount of toxic agent is impermeant to bacterial and non-bacterial cells in the absence of said antimicrobial agent and is only toxic upon entry into the antibiotic resistant bacteria, thereby allowing the lethal amount of toxic agent to enter and kill the transiently permeabilized, antibiotic resistant bacteria.

10. A method of killing bacteria with a membrane impermeant toxic agent, comprising; contacting said bacteria with a sublethal dose of an antimicrobial agent in combination with a lethal amount of said membrane impermeant toxic agent, wherein the antimicrobial agent permeabilizes bacterial but not non-bacterial cells, and is present in an amount sufficient to transiently permeabilize the bacteria such that the bacteria maintain membrane potential, and wherein the toxic agent is selected from the group consisting of: a molecule having at least two positive charges, a molecule that binds nucleic acid, acridines, thiazines, phenanthridinium compounds, symmetrical cyanine dyes, asymmetrical cyanine dyes, and homo- and heterodimers thereof, wherein said lethal amount of membrane impermeant toxic agent is impermeant to bacterial and non-bacterial cells in the absence of said antimicrobial agent and is only toxic upon entry into the bacteria, thereby allowing the lethal amount of membrane impermeant toxic agent to enter and kill the transiently permeabilized bacteria.

11. The method of claim 10, wherein the bacteria are antibiotic resistant.

12. A method of killing bacteria selected from the group consisting of *S. aureus* and *M. luteus,* with a lethal amount of toxic agent sufficient to kill transiently permeabilized bacteria, comprising contacting said bacteria with amoxicillin at a concentration of about 1 to about 90% minimal inhibitory concentration of amoxicillin, in combination with a lethal amount of said toxic agent selected from the group consisting of: phenanthridinium compounds and unsymmetrical cyanine dye compounds, wherein the lethal amount of toxic agent is impermeant to the bacteria in the absence of the amoxicillin and wherein the amoxicillin transiently permeabilizes the bacteria, such that the bacteria maintains membrane potential, thereby allowing the lethal amount of toxic agent to enter and kill the transiently permeabilized bacteria.

13. A method of killing a pathogen with a modified toxic agent, comprising; contacting said pathogen with a permeabilizing compound and with a lethal amount of said modified toxic agent, wherein said lethal amount of modified toxic agent comprises a toxic agent that has been chemically modified such that the lethal amount of said modified toxic agent is impermeant to pathogen and host cells in the absence of the permeabilizing compound and said lethal amount of said modified toxic agent is only toxic upon entry into the pathogen, and wherein the permeabilizing compound permeabilizes pathogen but not host cells and is present in an amount sufficient to transiently permeabilize the pathogen such that the pathogen maintains membrane potential, thereby allowing the lethal amount of said modified toxic agent to enter and kill the transiently permeabilized pathogen.

\* \* \* \* \*